US006841153B1

(12) United States Patent
Chegini et al.

(10) Patent No.: US 6,841,153 B1
(45) Date of Patent: Jan. 11, 2005

(54) PREVENTION OF ADHESIONS

(75) Inventors: Nasser Chegini, Gainesville, FL (US); James Burns, Watertown, MA (US); Michael P. Diamond, Grosse Pointe, MI (US); Lena E. Holmdahl, Cambridge, MA (US)

(73) Assignees: University of Florida, Gainesville, FL (US); Wayne State University, Detroit, MI (US); Genzyme Corporation, Framingham, MA (US)

( * ) Notice: Subject to any disclaimer, the term of this patent is extended or adjusted under 35 U.S.C. 154(b) by 0 days.

(21) Appl. No.: 09/787,144

(22) PCT Filed: Oct. 1, 1999

(86) PCT No.: PCT/US99/23014

§ 371 (c)(1),
(2), (4) Date: Jul. 16, 2001

(87) PCT Pub. No.: WO00/20642

PCT Pub. Date: Apr. 13, 2000

Related U.S. Application Data

(60) Provisional application No. 60/102,869, filed on Oct. 2, 1998.

(51) Int. Cl.$^7$ ............... A61K 39/395; A61K 39/44; C07K 16/28
(52) U.S. Cl. ............... 424/145.1; 424/178.1; 530/388.24; 530/389.2; 530/391.1
(58) Field of Search ............... 424/146.1, 145.1, 424/178.1; 530/357.5, 385.76, 389.2, 388.24

(56) References Cited

U.S. PATENT DOCUMENTS

| | | |
|---|---|---|
| 5,744,442 A | 4/1998 | Richards et al. |
| 5,843,673 A | 12/1998 | Sharpe-Timms |
| 2001/0034327 A1 | 10/2001 | Brunner et al. |
| 2003/0096755 A1 | 5/2003 | Brunner et al. |
| 2003/0176332 A1 | 9/2003 | Olmarker |

OTHER PUBLICATIONS

Kahan BD. Immunosuppressive therapy. Curr Opin Immunol. 4(5):553–560, 1992.*

Ward PA, Mulligan MS. Blocking of adhesion molecules in vivo as anti–inflammatory therapy. Ther Immunol 1(3):165–171, 199.*

Menino, Jr. et al., Expression of Proteinases and Proteinase Inhibitors During Embryo–Uterine Contact in the Pig. Dev. Genetics 1997, vol. 21, pp. 68–74.

Stearns et al, Cytokine (IL–10–6) Induction of Tissue Inhibitor of Metalloproteinase 1 in Primary Human Prostate Tumor Cell Lines. Oncology Research. 1995, vol. 7, Nos. 3/4, pp. 173–181, especially p. 179, Figure 5.

Oh et al., Matrix metalloproteinase–9/Gelatinase B is Required for Process Outgrowth by Oligodendrocytes. J. of Neuroscience. Oct. 1, 1999, vol. 19, pp. 8464–8475.

Hsu et al., Colon carcinoma cells with inactive nm 23 show increased motility and response to motility factors. Carcinogenesis. 1995, vol. 16, No. 9, pp. 2259–2262.

Alexander, C.M. and Werb, Z. "Targeted Disruption of the Tissue Inhibitor of Metalloproteinases Gene Increases the Invasive Behavior of Primitive Mesenchymal Cells Derived from Embryonic Stern Cells in Vitro" *J. Cell Biol.*, 1992, 118:727–739.

Chegini, N. et al., "Comparative Analysis of Matrix Metalloproteanase (MMP–1), Tissue Inhibitor of MMP (TIMP–1) and MMP–1/TIMP–1 Complex Expression in Intraperitoneal Environment and Their Relation to Adhesion Development" *Fertility and Sterility*, mailed to subscribers Sep. 1998, 70(No. 3, Suppl. 1):S26–S27, abstract.

Forough, R. et al., "Generating Antibodies Against Secreted Proteins Using Vascular Smooth Muscle Cells Transduced with Replication–Defective Retrovirus" *BioTechniques*, 1996, 20:694–701.

Khokha, R. et al., "Antisense RNA—Induced Reduction in Murine TIMP Levels Confers Oncogenicity on Swiss 3T3 Cells" *Science*, 1989, 243(4893):947–950.

* cited by examiner

Primary Examiner—Patrick J. Nolan
Assistant Examiner—Maher Haddad
(74) Attorney, Agent, or Firm—Saliwanchik, Lloyd & Saliwanchik

(57) ABSTRACT

Methods for the prevention of adhesion formation involve the administration of therapeutic formulations to a patient which include antibodies to TIMP-1 or TIMP-1 antisense oligonucleotides. The formulations can also include suitable carriers, such as a hyaluronic acid matrix, for optimal administration. The treatment procedure can be initiated and monitored by a diagnostic procedure which involves the detection of elevated levels of TIMP-1 in a patient.

7 Claims, 6 Drawing Sheets

PREVENTION OF ADHESIONS

This application is a National Stage of International Application Number PCT/US99/23014, filed Oct. 1, 1999, which claims the benefit of U.S. provisional patent application Ser. No. 60/102,869, filed Oct. 2, 1998.

BACKGROUND OF THE INVENTION

It is well established that post-operative adhesions develop in the vast majority of patients after surgery. Injury or inflammation in the peritoneal cavity produces a fibrous exudate. As a result, the serosal surfaces stick together. The fibrous exudate may be absorbed or invaded by fibroblasts to form a permanent fibrous adhesion.

Removal of fibrin before it is invaded by fibroblasts prevents the formation of permanent fibrous adhesions. Removal of fibrin occurs due to the fibrinolytic activity of the peritoneal cavity. Fibrinolytic activity can vary as a result of surgery. Fibrinolytic activity is absent from a peritoneal wound during the first 48 hours after surgery. However, there is a gradual increase after this time up to 8 days when the peritoneum heals. The source of the fibrinolytic activity is found in the mesothelial cells. It is postulated that the absence of definitive mesothelial cells with their associated fibrinolytic activity may facilitate adhesion formation by allowing fibroplasm to occur before definitive mesothelial cells have grown between and separated the two opposed surfaces of a fibrinous adhesion.

The molecular events underlying peritoneal wound healing and development of fibrous adhesions are complex and multifactoral. The cascade of events that leads to peritoneal wound repair in many aspects resembles those that occur during skin wound healing, which is characterized by inflammation, cellular migration, proliferation, phenotypic differentiation and tissue remodeling. Tissue remodeling involves deposition and degradation of the extracellular matrix which are highly regulated processes, occurs throughout wound repair, and are influenced by a host of locally expressed growth factors, cytokines and eicosanoids. The extracellular matrix is a dynamic component capable of modulating various cellular activities including cell—cell interaction, proliferation, differentiation and sequestering potent biological response modifiers from the wound environment. In addition, it has become clear that excess production and deposition of the extracellular matrix is a key factor in producing tissue fibrosis throughout the body including the development of peritoneal adhesions.

It has been suggested that serine proteases and metalloproteinases not only play a critical role in various stages of normal wound repair, but are involved in enhanced breakdown of the major components of the extracellular matrix in pathological wound healing. Matrix metalloproteinases ("MMPs") are members of a family of zinc proteases which hydrolyze various components of the extracellular matrix such as collagens, fibronectin, laminin, elastin and protoglycans. Seventeen different MMPs have been isolated and characterized, which based on their substrate specificity are divided into several subgroups: collagenases (MMP-1, MMP-8, MMP-13), gelatineses (MMP-2 and MMP-9), stromalysins (MMP-3, MMP-7, MMP-10, MMP-11), matrilysins (MMP-9), and the newly discovered membrane-type MMPs (MT-MMP1 to MT-MMP-4 or MMP-14 to MMP-17). The catalytic activity of MMPs is regulated at least in part by a group of proteins referred to as tissue inhibitors of matrix metalloproteineases or TIMPs. Four TIMPs have been identified and are referred to as TIMP-1, TIMP-2, TIMP-3 and TIMP-4.

A coordinated expression and balance between the production of MMPs and TIMPs is an important step in tissue remodeling. In general, MMPs are not expressed constitutively in vivo in adult tissues, but they are induced in response to various stimuli including proinflammatory cytokines, growth factors and hormones. MMPs are also induced in tissues that normally undergo extensive remodeling such as the endometrium during the menstrual cycle and wounds during healing. Furthermore, an important feature of the MMPs is that they are produced as inactive proenzymes and require activation, which is achieved by various factors including several serine proteineases such as plasmin, trypsin and neutrophil elastase. In contrast, the expression of TIMPs is wide spread in many tissues and is regulated in co-ordination with MMPs. TIMP-1 and TIMP-2 inhibit the activity of all MMPs by forming a high affinity complex in a 1:1 ratio. In addition to inhibiting the MMPs activity, TIMPs have also been shown to have growth factor like activity by stimulating cell growth.

Thus, for normal peritoneal healing to occur, the availability of these molecules must be optimal, precise, and synchronized. Inhibition, interruption, or excess expression of these molecules seems to be responsible for failure in normal healing, resulting in either impairment or excess tissue formation (adhesion development). Although the role of growth factors, cytokines, eicosanoids and serine proteinases have been investigated in relation to peritoneal wound repair and adhesion formation, there is no information currently available in respect to the expression of MMPs and TIMPs in the peritoneal environment.

The formation of intraperitoneal fibrous adhesions is a complex process that involves migration and mitosis of a variety of cell types, including inflammatory cells, mesothelial cells, and fibroblasts. Peptide growth factors and their receptors may play key roles in regulating many aspects of adhesion formation. Growth factors, such as epidermal growth factor (EGF), and transforming growth factor-$\beta$ (TGF-$\beta$) may directly influence adhesion formation.

SUMMARY OF THE INVENTION

It has now been discovered that an unbalanced level of MMP-1 and TIMP-1 in a human subject, high TIMP-1 expression, and the association of a major portion of MMP-1 in complex with TIMP-1 may be major contributing factors in the peritoneal environment by providing a favorable condition for adhesion development. This discovery has lead to the development of novel methods for treating surgical adhesions, for diagnosing the probability of developing adhesion formation, and for preparing pharmaceutical formulations for reducing or preventing adhesions.

In one particular aspect of the invention, a method for the prevention or remediation of surgical adhesions comprises treating a patient at risk of having such adhesions with a therapeutic formulation selected form the group consisting of antibodies to TIMP-1 and TIMP-1 antisense oligonucleotides. Treatment with TIMP-1 antibodies results in the alteration of local levels of both TIMP-1 and MMP. Antisense oligonucleotides can be targeted to a specific gene's mRNA destruction to inhibit the synthesis of proteins.

In another aspect of this invention, antibodies to TIMP-1 are disclosed and used to formulate a therapeutic formulation for the treatment or prevention of surgical adhesions. The antibodies can be polyclonal antibodies, monoclonal antibodies or Fab fragments. The formulation can include suitable carriers and adjuvants. A particularly preferred carrier is a hyaluronic acid matrix, which can be derivatized, underivatized or cross-linked.

An additional aspect of this invention involves a method for the detection of a predisposition in a subject to adhesion formation which comprises the detection of elevated levels of TIMP-1 in a human subject. Once detected, the predisposition for adhesion formation can then be treated using the procedure of this invention.

DETAILED DESCRIPTION OF THE INVENTION

Figure 1:
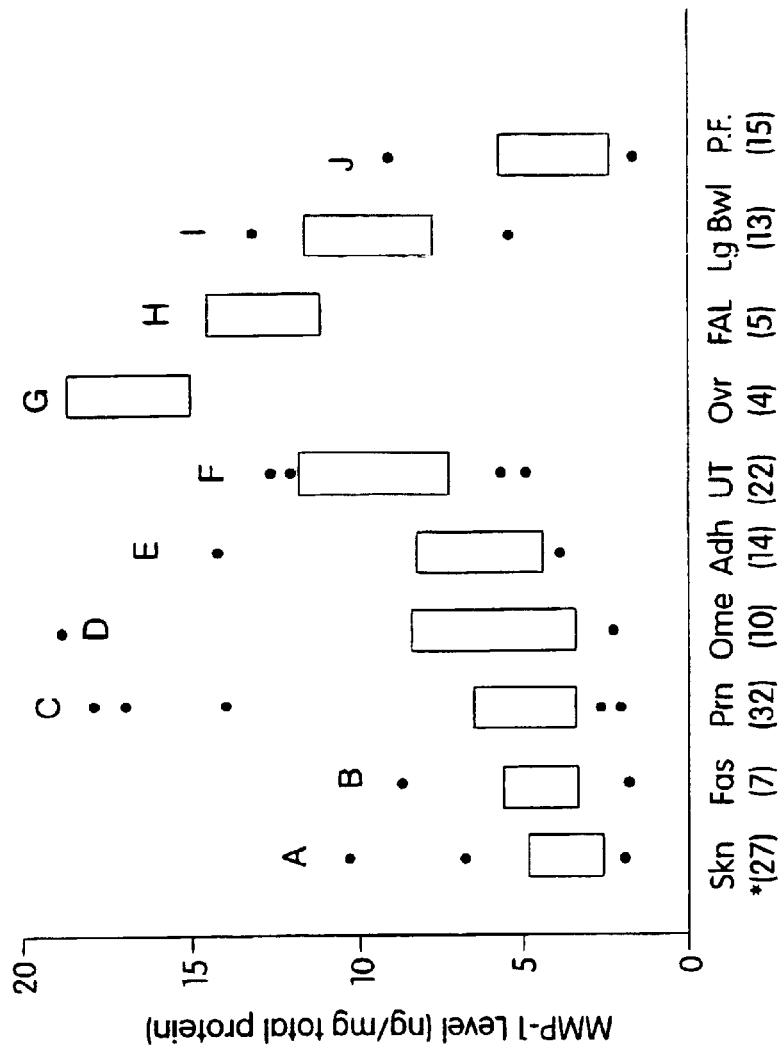
FIG. 1 is a diagram showing the expression of MMP-1 in intraperitoneal tissue.
Figure 2:
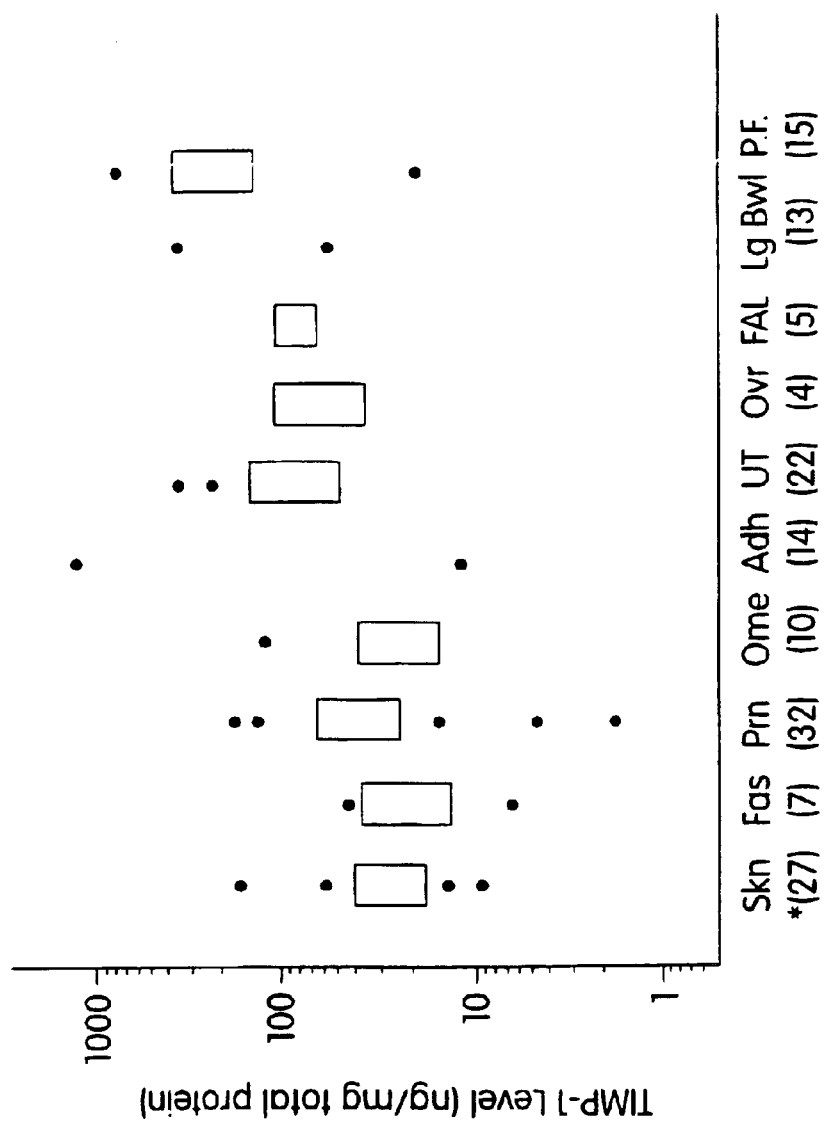
FIG. 2 is a diagram showing the expression of TIMP-1 in intraperitoneal tissue.
Figure 3:
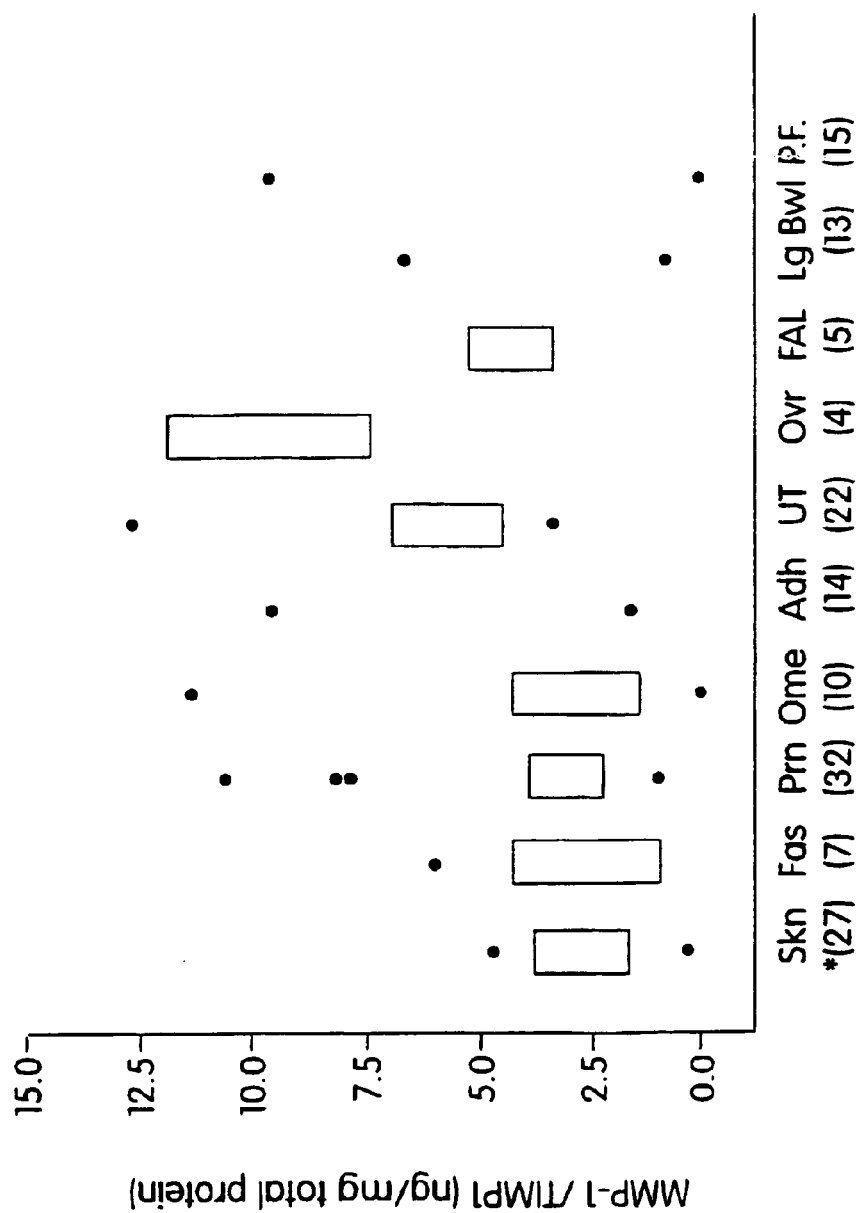
FIG. 3 is a diagram showing the co-expression of MMP-1 and TIMP-1 in intra-peritoneal tissue.
Figure 4:
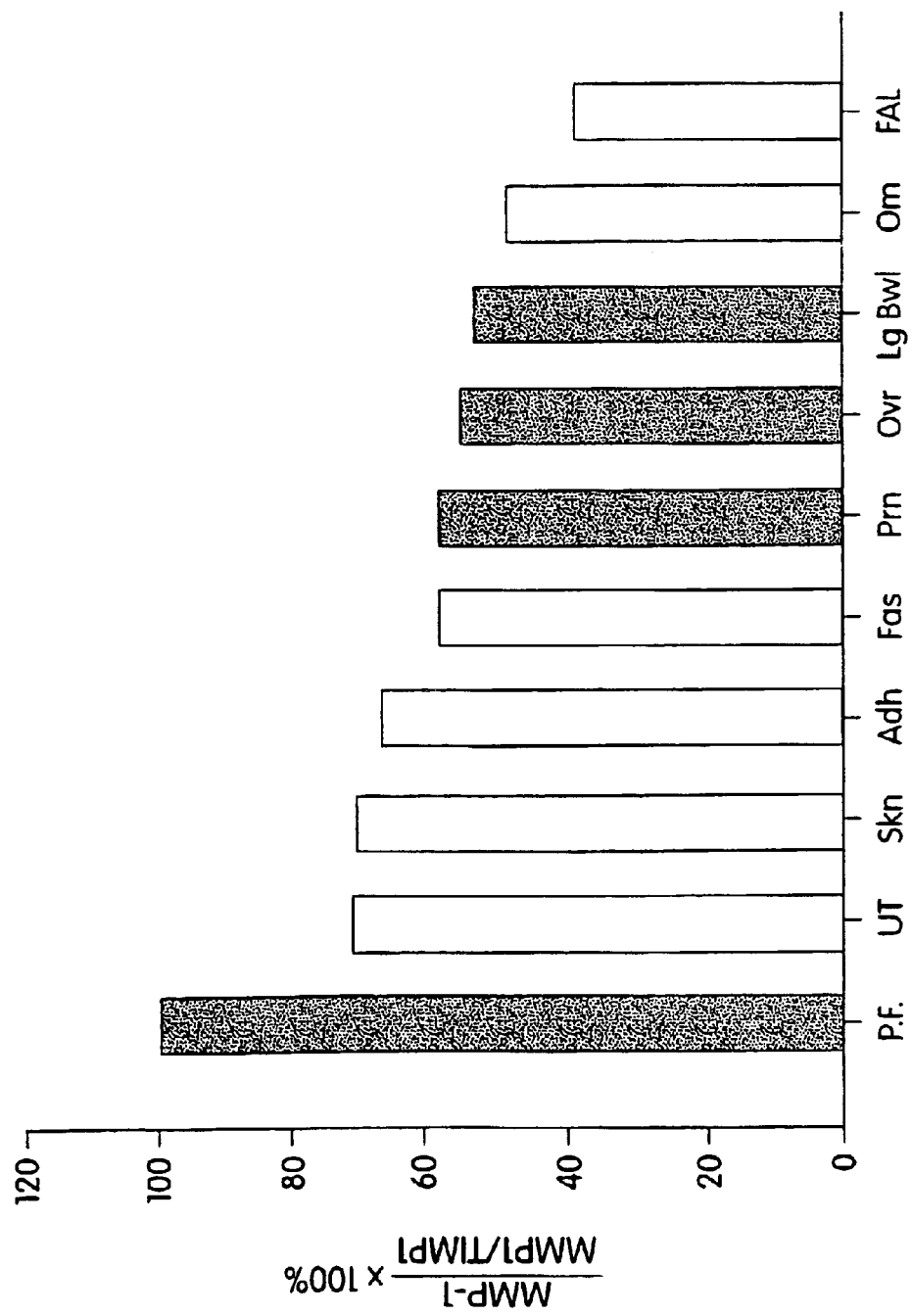
FIG. 4 is a diagram showing MMP-1 production levels.
Figure 5:
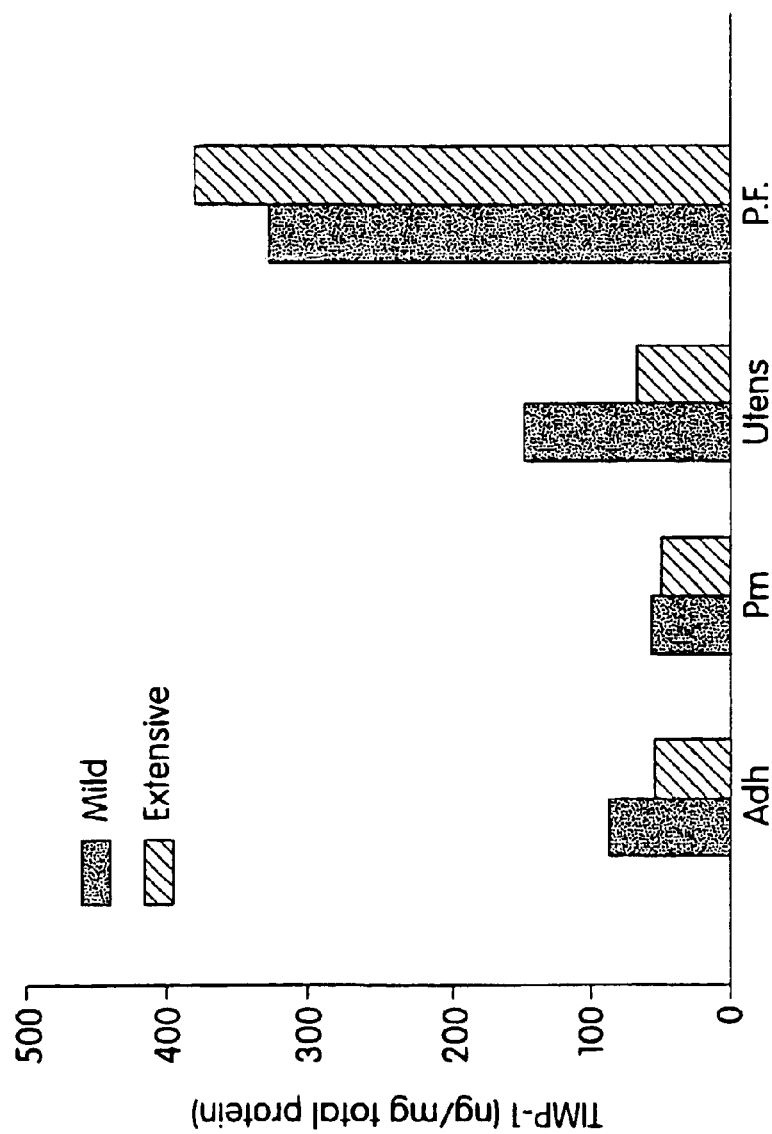
FIG. 5 is a diagram showing the comparative levels of TIMP-1 production in mild as compared to extensive adhesions.
Figure 6:
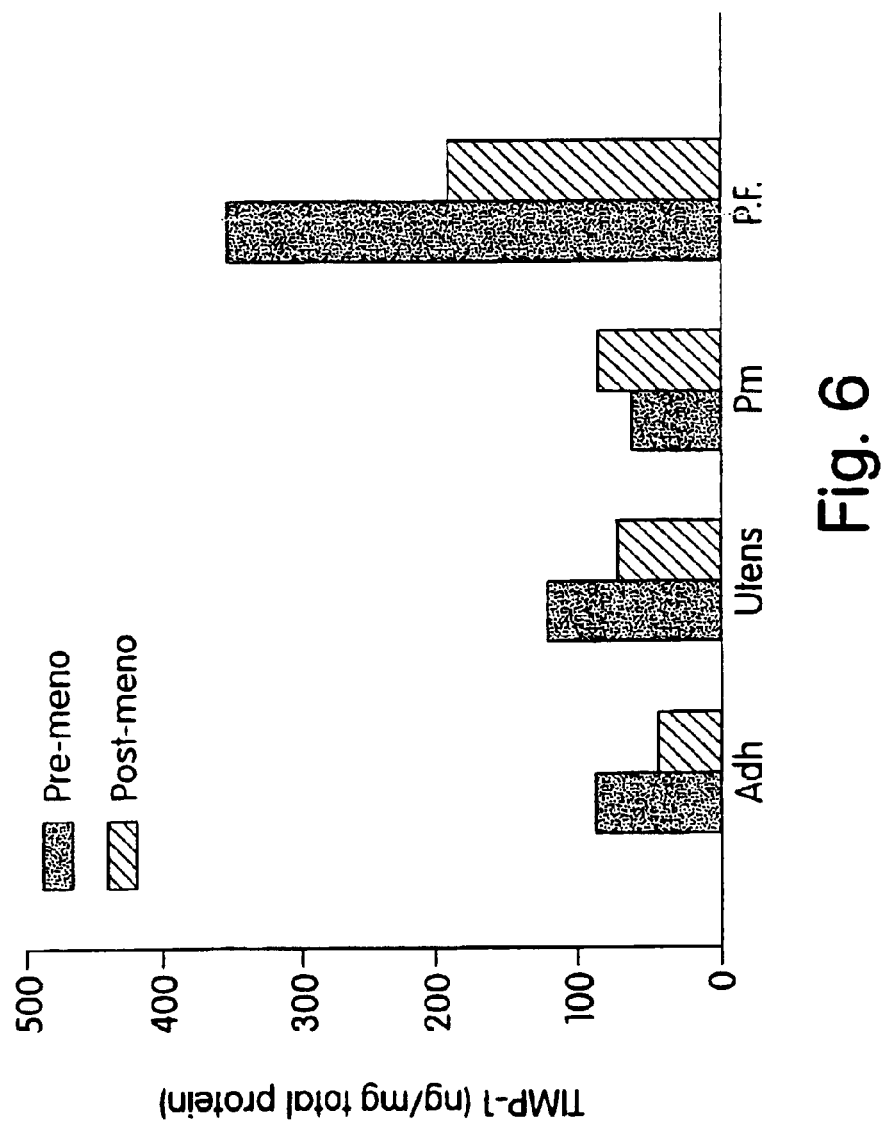
FIG. 6 is a diagram showing the comparative levels of TIMP-1 expression in the female peritoneal environment for both pre-menopausal and post-menopausal women.

An important area for the prevention of adhesion formation is the modulation of growth factors and cytokines. The present invention provides for the first time a comparative analysis of the level of expression of MMP-1, TIMP-1 and MMP-1/TIMP-1 in various tissues within the peritoneal cavity and peritoneal fluids of patients who were undergoing pelvic/abdominal surgical procedures. The results indicate that interstitial collagenase or MMP-1, which degrades type I, II, III and VII collagens, is expressed at a significantly higher level in ovaries and fallopian tubes compared to skin, fascia, parietal peritoneum, omentum, uterus, and large bowl, as well as fibrous adhesions, with lowest levels associated with skin. Also, in peritoneal fluid the level of MMP-1 is low and comparable to that detected in skin, which under normal conditions expresses low to undetectable levels of MMPs. Comparatively, adhesions express a moderate level of MMP-1, which is significantly lower than in ovaries and higher than in skin.

In contrast to MMP-1, the expression of TIMP-1 in tissues was highest in adhesions with ranges from 2 to 8 fold higher, but approximately 1.5 fold lower than that detected in peritoneal fluid. These results suggest that in the peritoneal environment, tissues such as ovaries, fallopian tubes and uterus express higher levels of MMP-1 and TIMP-1. The results are consistent without regard to the cause of trauma, i.e. ovaries, fallopian tubes and uterus appear to be more susceptible to adhesion formation following trauma, irrespective of whether it is caused by physical, cytotoxic, inflammatory or immunological factors. This may be due to high levels of TIMP-1 expression which inactivates all the MMPs including MMP-1 by forming complexes with TIMPs in a 1:1 ratio.

In support of this conclusion, we observed that in patients with extensive adhesions, the level of TIMP-1 expression was substantially higher than those with moderate or mild adhesions. Although there appears to be a trend for higher TIMP-1 expression in patients with extensive adhesions, due to variability in the number of patients within each group and inconsistency in the type of tissues collected during sampling, it is difficult to reach a conclusion at the present time regarding the levels in patients with and without adhesions. The results further indicate that the level of MMP-1/TIMP-1 complex in the ovaries and uterus is the highest, compared to other tissues, and corresponds to 55 to 70% of total MMP-1 level expressed in these tissues. Such a relationship between the level of MMP-1/TIMP-1 complex, and the level of total MMP-1 was also observed in other tissues, with levels ranging from 37% to 69%.

Peritoneal fluid is also regarded to pay a key role in development of adhesion formation, due to the presence of various factors. With regard to the peritoneal fluid, MMP-1 and MMP-1/TIMP-1 complex was low compared to their tissue levels. However, peritoneal fluid contained the highest level of TIMP-1. Furthermore, the adhesions also express a low level of MMP-1 and MMP-1/TIMP-1 complex, while they expressed the second highest level of TIMP-1 compared to other tissues. It would appear that 100% of total MMP-1 detected in peritoneal fluids and 65% in the adhesions was in complex with TIMP-1. This suggests that the role of peritoneal fluid in the context of adhesion formation favors matrix deposition rather than degradation, and is consistent with the clinical impression. Thus, once an adhesion develops, it will persist and does not spontaneously resolve. Furthermore, this milieu favors extracellular matrix deposition, and is consistent with clinical reports that adhesions become thicker and more dense over time. Although the adhesions examined in this report are mature and far less dynamic, our data suggest that they appear to exist under a molecular environment which prevents proteolytic enzyme degradation by MMPs. Furthermore, in addition to inhibiting the activity of the MMPs, TIMP-1 has been demonstrated to have growth factor like activity by stimulating cell growth. Because of the high content of TIMP-1 in the peritoneal fluid, TIMP-1 may have a stimulatory effect on cell growth, including fibroblasts which migrate into the site of injury at the initial stage of adhesion formation.

Potentially, several growth factors, cytokines and eicosanoids, which are expressed by these tissues and present in the peritoneal fluid, can regulate the expression of MMPs and TIMPs. In addition, in tissues such as the uterus and the ovary, the expression of MMPs and TIMPs has been shown to be regulated by ovarian steroids and gonadotropins, respectively. In this respect, MMPs have been associated with endometrial breakdown during the menstrual cycle and progesterone has been reported to inhibit the expression of a selective number of MMPs in this tissue. Among the growth factors and cytokines, it is well established that excess production of TGF-$\beta$ in various tissues leads to pathological fibrosis including peritoneal adhesions. In general, the effect of TGF-$\beta$ on tissue fibrosis occurs through increasing synthesis and deposition of extracellular matrix and decreasing their degradation through differential regulation of MMPs and TIMPs. In fibroblasts, TGF-$\beta$ inhibits MMP-1, stimulates TIMP-1 expression and prevents plasmin generation by increasing the expression of plasminogen activator inhibitor (PAI-1), allowing the unopposed deposition of extracellular matrix. Fibrous adhesions and peritoneal fluid express elevated levels of TGF-$\beta$1 during the early stages of wound repair and treatment of myometrial smooth muscle cells and adhesion fibroblasts with TCF-$\beta$ result in differential regulation of $\alpha$1 procollagen, fibronectin, TIMP-1 and MMP-1 mRNA expression in these cells. Furthermore, TGF-$\beta$1 has been shown to suppress the expression of MMP-3 (steromlysin 1) in fibroblasts and MMP-7 (Matrilysin) in endometrial epithelial cells. It has also been reported that resting keritinocytes in normal skin do not express MMP-1 and MMP-3.

It appears that for normal healing to proceed, the expression and availability of the molecules must be optimal, precise and synchronized. Inhibition, interruption or excess expression of these molecules seem to be responsible for the failure of normal healing, either impairment (nonhealing) or excess tissue formation (adhesion development). In this regard our data provide the first evidence that an unbalanced level of MMP-1 and TIMP-1, high TIMP-1 expression, and association of a major portion of MMP-1 in complex with TIMP-1 may be major contributing factors in the peritoneal environment which provide a favorable condition leading to adhesion development.

To test our hypothesis, we assessed whether MMP and TIMP expression is altered in patients who do or do not have adhesions, as well as whether there is tissue variation within the peritoneal environment which may influence likelihood of adhesions. The present study comparatively examined the expression of MMP-1, TIMP-1 and MMP-1/TIMP-1 complex in various intaperitoneal tissues including parietal peritoneum, uterus, fallopian tube, ovary, bowel, omentum and adhesions as well as in skin, fascia, and peritoneal fluids in patients who were undergoing abdominal/pelvic surgical procedures.

EXAMPLE

Tissue specimens including skin, fascia, parietal peritoneum, uterus, fallopian tube, ovary, large bowel, omentum and adhesion, as well as peritoneal fluids were collected from patients (N=55) who were undergoing abdominal/pelvic surgical procedures. Peritoneal fluids were excluded if the fluids became contaminated with blood during the collection. Thus, peritoneal fluid from 15 patients were analyzed. The collection of the tissues and peritoneal fluid from these patients was approved by the Institutional Review Board from each individual institution prior to initiation of the study. All patients gave informed written consent prior to tissue collection.

The patient's pelvic findings at surgery were used to asses the type of adhesions. The extent of adhesion formation was determined and classified based on their severity as previously described. In female patients, adhesions involving only a small area, usually the tubes and ovaries, and lysed with ease were categorized as minor, adhesions involving larger areas were classified moderate, and more vascular and cohesive adhesions were categorized as extensive. In male patients, adhesions were categorized in a similar manner, although the patients were undergoing various gastrointestinal surgical procedures.

After collection, the tissues pieces were divided into multiple portions and one portion was subjected to extraction of MMPs and TIMPs according to the protocol described in the ELISA kits and established in our laboratory. Prior to the ELISA assay, the total protein content of the tissue extracts were determined using a standard protein assay kit (Bio-Rad, Hercules Calif.). An equal amount of the tissue extracts and peritoneal fluids were assayed using human specific ELISA's for MMP-1, TIMP-1 and MMP-1/TIMP-1 complex with limits of detection of 1.7, 1.25 and 1.5 ng/ml, respectively, measuring the total MMP-1 (free and in complex with TIMP-1, but not with α2-macroglobulin), total TIMP-1 (free and in complex with MMPs) and MMP-1/TIMP-1 complex (activated MMP-1 that has subsequently been complexed with TIMP-1). The ELISA kits were purchased from Oncogen Sciences (Cambridge Mass.) and used according to the procedures provided by the manufacturers. Data are expressed as mean ±SEM and significance was defined as $P<0.05$. The data were statistically analyzed using one way analysis of variance (ANOVA) and Dunn's multiple test and presented as ng of MMPs or TIMPs/ mg of total protein. Of the 55 patients, 45 were female and 10 were male, ranging in age from 24 to 83. Among the female patients, 13 were postmenopausal and 32 were premenopausal, of whom 23 had previous invasive and noninvasive pelvic surgical procedures which included cesarean sections, bilateral tubal intervention, appendectomy, ovarian cystectomy, hysterectomy and/or treatment for endometriosis. Based on each premenopausal patient's last menstrual period and endometrial histology, 9 patients were in the proliferative phase and 23 were in the secretory phase of the menstrual cycle.

Irrespective of the patients age, gender, medical diagnosis and pervious medical history, all the tissue extracts and peritoneal fluids express MMP-1, TIMP-1 and MMP-1/TIMP-1 complex. However, the tissues and peritoneal fluids express a significantly higher TIMP-1 compared to MMP-1 or MMP-1/TIMP-1, with ranges from 2 to 10 fold higher ($P<0.05$). There were also significant variations in the levels of MMP-1, TIMP-1 and MMP-1/TIMP-1 expression in tissues and peritoneal fluid within and among the patients, ranging from 2 fold higher for MMP-1 and MMP-1/TIMP-1 and up to 10 fold higher for TIMP-1 ($P<0.05$). The ovaries appeared to express a significantly higher level of MMP-1, followed by fallopian tube, large bowel, uterus, omentum, adhesion, parietal peritoneum, fascia, peritoneal fluid arid skin ($P<0.001$). In contrast, the highest level of TIMP-1 expression was found in peritoneal fluid, followed by adhesions, large bowel, uterus, fallopian tube, ovary, peritoneum, omentum, skin and fascia ($P<0.01$).

In the adhesions, the level of TIMP-1 expression was substantially higher in patients with extensive adhesion, compared to moderate to mild adhesion, but was not significant. In general, the mean levels of TIMP-1, but not MMP-1 and MMP-1/TIMP-1 complex were substantially higher in all the tissues and peritoneal fluids of premenopausal patients compared to postmenopausal patients. Comparatively, the levels of MMP-1/TIMP-1 complex expression were similar to that of MMP-1 in the tissue extracts and peritoneal fluids, with highest level expression found in the ovary ($P<0.05$).

With respect to the type of adhesions, the peritoneal fluid of patients with extensive adhesions had a substantially higher TIMP-1. Compared to peritoneal fluid, parietal peritoneum from all patients expressed more MMP-1, but significantly lower TIMP-1 ($P<0.003$), with both expressing equal amounts of MMP-1/TIMP-1 complex. Adhesions and skin expressed the lowest MMP-1 and TIMP-1 compared to other tissues. However, despite variability among the number of tissue samples, it appears that in patients with extensive adhesions, the adhesions expressed substantially more TIMP-1 than those with moderate adhesions. Essentially, most if not all the MMP-1 appears to be associated in complex with TIMP-1, both in peritoneal fluid and in all the tissues examined, ranging from 38% (fallopian tube) to 100% (peritoneal fluid).

What is claimed is:

1. A method for reducing surgical adhesion formation, comprising administering a therapeutic formulation comprising TIMP-1 antibodies, or Fab fragments thereof, to a patient at risk of surgical adhesion formation, wherein the therapeutic formulation is administered in an amount effective to reduce the local level of TIMP-1 and surgical adhesion formation.

2. The method of claim 1, wherein the therapeutic formulation comprises TIMP-1 antibodies, and wherein the TIMP-1 antibodies are monoclonal antibodies.

3. The method of claim 1, wherein the therapeutic formulation comprises TIMP-1 antibodies, and wherein the TIMP-1 antibodies are polyclonal antibodies.

4. The method of claim 1, wherein the therapeutic formulation further comprises a suitable carrier.

5. The method of claim 4, wherein the carrier is hyaluronic acid.

6. The method of claim 1, wherein the surgical adhesion is a peritoneal adhesion.

7. The method of claim 1, wherein the surgical adhesion is a surgical adhesion of intra-peritoneal tissue selected from the group consisting of parietal peritoneum, uterus, fallopian tube, ovary, bowel, and omentum.

* * * * *

UNITED STATES PATENT AND TRADEMARK OFFICE
CERTIFICATE OF CORRECTION

PATENT NO. : 6,841,153 B1
DATED : January 11, 2005
INVENTOR(S) : Nasser Chegini, et al.

It is certified that error appears in the above-identified patent and that said Letters Patent is hereby corrected as shown below:

<u>Column 4,</u>
Line 8, "to pay a key" should read -- to play a key --.
Line 59, "TCF-β" should read -- TGF-β --.

Signed and Sealed this

Seventeenth Day of May, 2005

JON W. DUDAS
*Director of the United States Patent and Trademark Office*